United States Patent
Goodall et al.

(10) Patent No.: US 9,352,080 B2
(45) Date of Patent: May 31, 2016

(54) BURETTE

(75) Inventors: Stephen Francis Goodall, Carindale (AU); Angelo John Maltabes, Gladstone (AU); Geoffrey Daniel Daly, Sherwood (AU)

(73) Assignee: ANALYTICA LIMITED, Queensland (AU)

( * ) Notice: Subject to any disclaimer, the term of this patent is extended or adjusted under 35 U.S.C. 154(b) by 1558 days.

(21) Appl. No.: 12/090,014

(22) PCT Filed: Oct. 12, 2006

(86) PCT No.: PCT/AU2006/001495
§ 371 (c)(1),
(2), (4) Date: Jul. 18, 2008

(87) PCT Pub. No.: WO2007/041787
PCT Pub. Date: Apr. 19, 2007

(65) Prior Publication Data
US 2009/0287152 A1   Nov. 19, 2009

(30) Foreign Application Priority Data
Oct. 13, 2005   (AU) .............................. 2005905661

(51) Int. Cl.
*A61M 5/14* (2006.01)
*A61M 5/40* (2006.01)
*A61M 5/168* (2006.01)

(52) U.S. Cl.
CPC ........... *A61M 5/1411* (2013.01); *A61M 5/1408* (2013.01); *A61M 5/1412* (2013.01); *A61M 5/1685* (2013.01); *A61M 5/40* (2013.01)

(58) Field of Classification Search
CPC ... A61M 5/1411; A61M 5/40; A61M 5/1408; A61M 5/1412; A61M 5/1685
USPC .................................. 604/127, 247, 251–254
See application file for complete search history.

(56) References Cited

U.S. PATENT DOCUMENTS

| | | | |
|---|---|---|---|
| 3,465,784 A | 9/1969 | Cofoid | |
| 3,667,464 A | 6/1972 | Alligood, Jr. | |
| 3,949,745 A | 4/1976 | Howell | |
| 4,256,103 A | 3/1981 | Mylrea | |
| 4,449,976 A | 5/1984 | Kamen | |
| 4,640,306 A | 2/1987 | Fan | |
| 4,947,154 A | 8/1990 | Hwang | |
| 4,959,053 A * | 9/1990 | Jang ...................... | A61M 5/162 604/127 |

(Continued)

FOREIGN PATENT DOCUMENTS

| | | |
|---|---|---|
| GB | 2147087 A | 5/1985 |
| GB | 2178135 A | 2/1987 |

OTHER PUBLICATIONS

International Search Report for WO 2007/041787 A1 dated Apr. 19, 2007.

*Primary Examiner* — Emily Schmidt
*Assistant Examiner* — Lauren M Peng
(74) *Attorney, Agent, or Firm* — Carter, DeLuca, Farrell & Schmidt LLP

(57) ABSTRACT

A burette (10) to receive liquid from an intravenous supply (29) to deliver liquid to a patient via a tube (30). The burette (10) includes a hollow body (11) that is generally cylindrical configuration and that contains a float valve (24). Liquid level in the chamber (12) of the body (11) regulates liquid level within the chamber (12) by engaging an inlet passage (36) or an outlet tube (25).

8 Claims, 6 Drawing Sheets

(56) References Cited

U.S. PATENT DOCUMENTS

| | | | | |
|---|---|---|---|---|
| 5,415,325 A | * | 5/1995 | Shu | A61M 5/1411 137/399 |
| 5,868,715 A | * | 2/1999 | Tung | A61M 5/40 604/245 |
| 5,967,490 A | * | 10/1999 | Pike | A61M 39/26 251/149.1 |
| 6,213,986 B1 | * | 4/2001 | Darling, Jr. | A61M 5/1411 137/423 |
| 6,569,116 B1 | * | 5/2003 | Wang | 604/127 |
| 6,641,559 B2 | * | 11/2003 | Guala | 604/127 |
| 2003/0158526 A1 | | 8/2003 | Huang | |

\* cited by examiner

BURETTE

TECHNICAL FIELD

The present invention relates to burettes and more particularly but not exclusively to medical burettes used to administer intravenous liquids.

BACKGROUND OF THE INVENTION

Australian Patent No. 689324 (equivalent to U.S. Pat. No. 5,885,532) describes a medical burette that controls the flow from an intravenous liquid supply to the patient, while providing for the delivery of secondary liquids via a septum or the like.

The above device is complex in its structure and therefore is relatively expensive to manufacture.

A further disadvantage of the above discussed burette occurs when the burette is to be used to dispense a medication. In such a use, delivery of liquid from an IV bag is terminated. Liquid is still delivered from the burette until the outlet is closed. However when the outlet is closed there is still considerable residue liquid in the burette. The medication is then added with the effect that the medication is substantially diluted by the residue liquid. When the medication has been delivered and again the outlet closed by the drop in fluid in the burette, a significant portion of the medication is still retained in the burette. Accordingly not only is the medication diluted, but the full medication is not delivered.

OBJECT OF THE INVENTION

It is the object of the present invention to overcome or substantially ameliorate the above disadvantage.

SUMMARY OF THE INVENTION

There is disclosed herein a burette including:
an elongated hollow body having a longitudinal axis that is to be generally vertically oriented during use, the body including a chamber to receive a liquid to be dispensed by the burette;
an inlet passage extending inwardly of the chamber so as to terminate with an end extremity in the chamber via which liquid is delivered to the chamber;
an outlet extending from the chamber, the outlet being located below the inlet extremity; and
a float valve located between the inlet passage and outlet and movable therebetween in response to changing liquid levels in the chamber, the float valve having a recess to hold liquid, the recess being vertically aligned with said extremity so that when liquid level in said chamber is above a predetermined level said extremity is located below liquid level in said recess to at least inhibit flow to said chamber through said passage, with the liquid level in said chamber falling below a predetermined level causing said float valve to engage said outlet to close said outlet to prevent further liquid from leaving said chamber.

Preferably, said inlet passage is provided by a tube.

Preferably, said chamber is vertically elongated with said inlet further including a hollow stem having a lower end within which said tube is mounted, with said stem having an upper end to which a supply of the liquid is to be attached.

Preferably, said burette includes a guide within which said valve float is located so as to be guided thereby for generally vertical movement between an upper position at which said extremity is located in said recess, and a lower extremity closing said outlet.

Preferably, the guide provides a socket within which the float is located when closing the outlet.

There is further disclosed herein a burette including:
an elongated hollow body having a longitudinal axis that is to be generally vertically oriented during use, the body including a chamber to receive a liquid to be dispensed by the burette;
an inlet passage extending inwardly of the chamber so as to terminate with an end extremity in the chamber via which liquid is delivered to the chamber;
an outlet extending from the chamber, the outlet being located below the inlet extremity; and
a float valve located between the inner passage and the outlet and movable therebetween in response to change in liquid levels in the chamber, the float valve having a first closure member to engage the end extremity to close said passage, and a second closure member to engage the outlet to close the outlet, so that upon the liquid level in the chamber being above a predetermined level said first closure member closes said end extremity, while when liquid level in the chamber falls below a further predetermined level, said second closure member closes said outlet.

Preferably, said first closure member and said second closure member are resilient pads.

Preferably, said valve float includes a hollow body to which said first and second closure members are attached.

Preferably, said first and second closure members are aligned along said axis.

Preferably, said second closure member directly engages said outlet.

In an alternative preferred form, said second closure member provides a seal surrounding said outlet to thereby isolate said outlet from said chamber so that said outlet is effectively closed.

BRIEF DESCRIPTION OF THE DRAWING

A preferred form of the present invention will now be described by way of example with reference to the accompanying drawings wherein.

DETAILED DESCRIPTION OF THE PREFERRED EMBODIMENT

Figure 1:
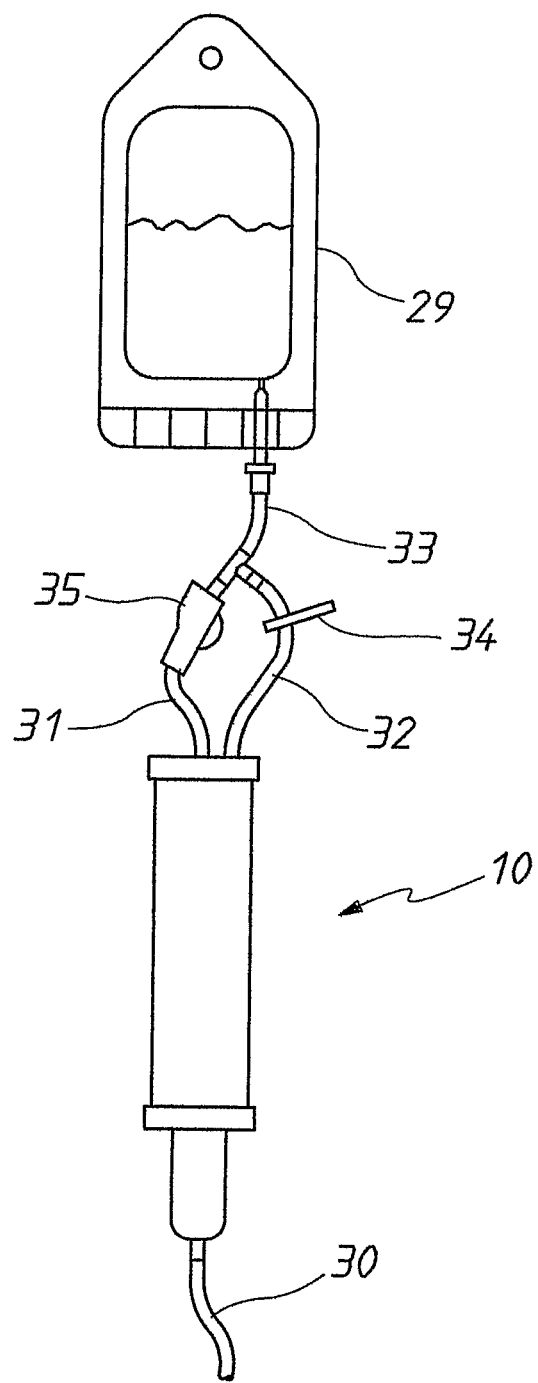
FIG. 1 is a schematic side elevation of a burette and an associated bag to provide a liquid, such as a saline solution.
Figure 2:
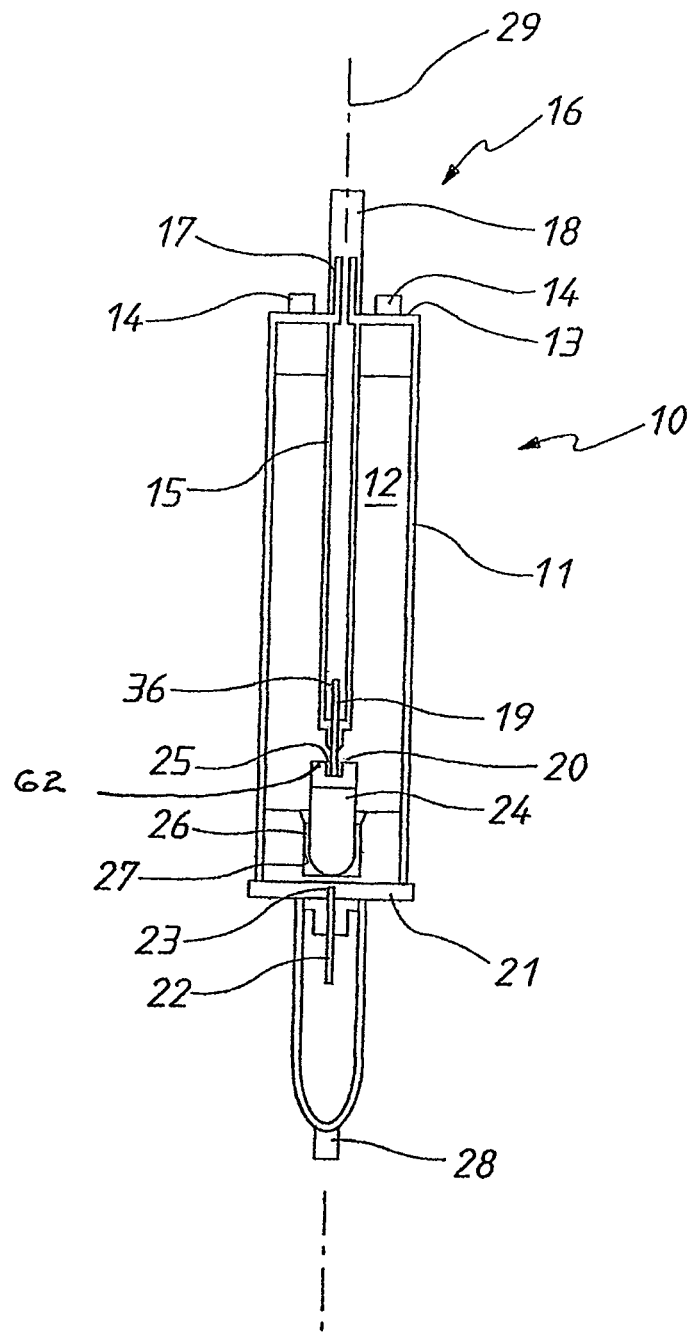
FIG. 2 is a schematic sectioned side elevation of the burette of FIG. 1.

In FIGS. 1 and 2 of the accompany drawings there is schematically depicted a burette 10. The burette 10 is a medical burette and is intended to receive liquid from an intravenous liquid supply (bag) 29, to deliver the liquid to a patient via a tube 30.

The burette 10 includes a hollow body 11 that is generally cylindrical and surrounds a chamber 12. Preferably the body 11 is transparent so that a user may observe the liquid level in the chamber 12.

The upper end of the body 11 is closed by means of a top wall 13 having ports 14 via which another liquid may be delivered to the chamber 12.

Mounted in the wall 13 is an inlet assembly 16 including an elongated hollow stem 15 terminating at its upper end with an extremity 17 with which there is engaged a flexible tube 18 extending to a supply of intravenous liquids, such as a flexible bag.

The assembly 16 further includes a tube 19 having a longitudinal passage 36. The tube 19 extends inwardly of the closed lower end of the stem 15 and projects outwardly from the stem 15 so as to have a lower extremity 20 of the passage 36 located in the chamber 12. In use liquid enters the stem 15 and ultimately flows through the tube 19 (passage 36) exiting via the extremity 20 to be delivered to the chamber 12.

The lower end of the body 11 is closed by means of a plug 21. Mounted in the plug 21 is an outlet tube 22 having an upper extremity 23.

Located between the extremities 20 and 23 so as to be generally vertically aligned with the tubes 19 and 22 is a valve float 24. The float 24 has a recess 25 that receives liquid that is located in the chamber 12.

The plug 21 has a recess 26 having side walls 27 that guide the valve float 24 in its movement that results from changing liquid levels in the chamber 12. The recess 26 acts as a socket to receive the float 24 to thereby minimise the residue liquid when the outlet tube 22 is closed.

The tube 22 delivers liquid to an outlet 28.

In operation of the above described medical burette 10, when liquid is delivered to the chamber 12 the float 24 rises until liquid in the recess 25 engages the extremity 20 to thereby prevent further flow through the tube 19. When liquid level in the chamber 12 falls below a predetermined level the float valve 24 engages the extremity 23 to close the outlet tube 24. The float valve 24 is guided in its vertical movement by means of walls 27 and is caused to move between its upper and lower positions by changing liquid levels in the chamber 12, so as to provide a regularly constant flow to the tube 22, that is the outlet 28.

Preferably the burette 10 is adapted to be suspended so as to have a longitudinal axis 29 that is generally vertically oriented.

The burette 10 is attached to the bag 29 by tubes 31 and 32 that are arranged in parallel and are connected to the bag outlet by means of a tube 33. The tube 32 is attached to one of the ports 14 to aid in the initial charging of the burette 10. Preferably the tube 32 would have associated with it a clamp 34 that could be operated to close the tube 32. An adjustable clamp 35 is also applied to the tube 31 to aid in regulating the flow therethrough.

Figure 3:
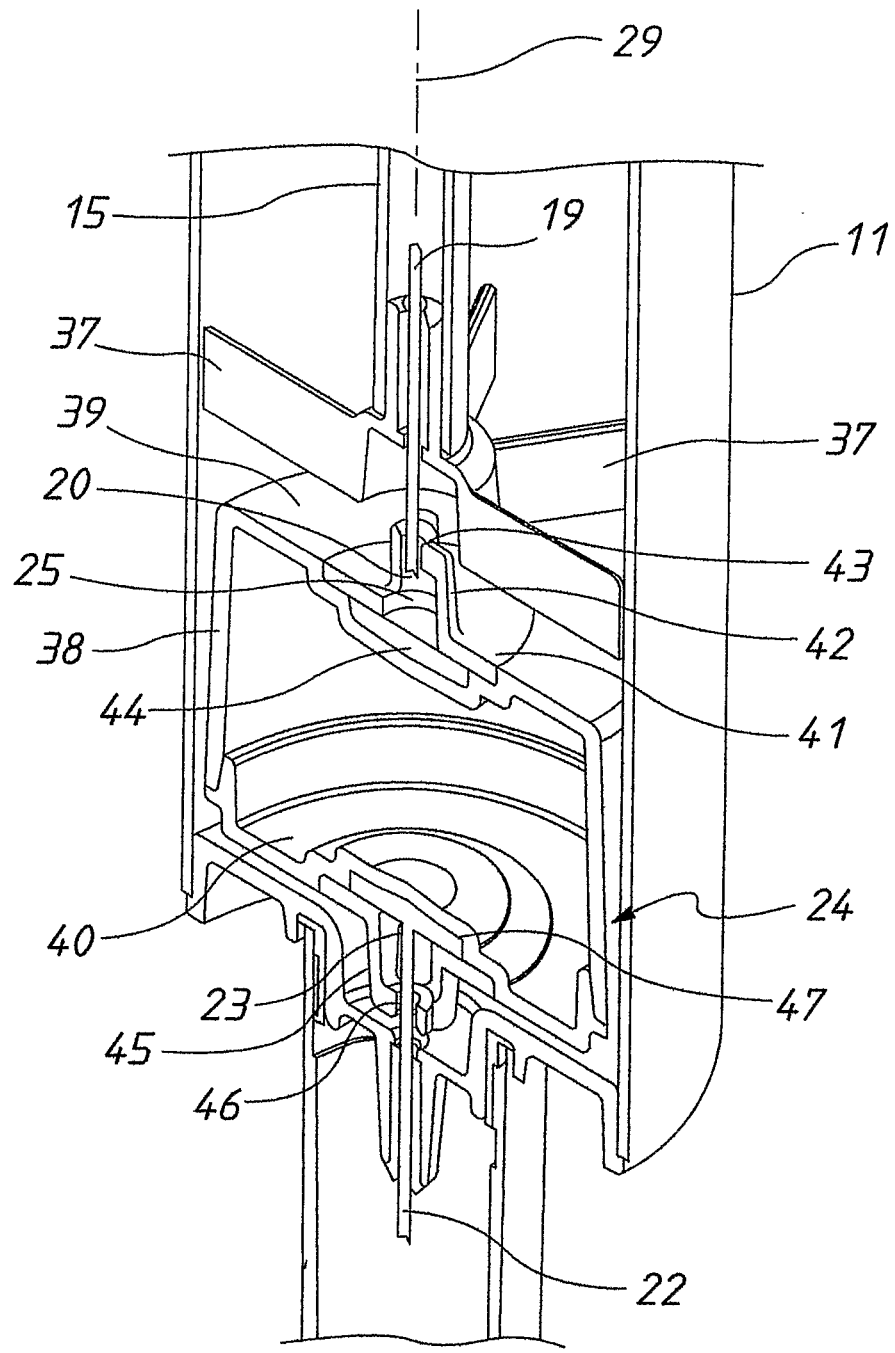
FIG. 3 is a schematic sectioned side elevation of a modification of the burette of FIG. 2.

In FIG. 3 there is schematically depicted a modification of the burette 10 of FIGS. 1 and 2. In this embodiment the stem 15 is maintained in position at its lower end by a plurality of fins 37 that extend radially from the lower end of the stem 15 to gauge the internal surfaces of the body 11.

The float valve 24 has a frusto-conical longitudinal wall 38 that converges upwardly toward the axis 29, with the wall 38 joining a top wall 39 and a bottom wall 40, with the walls 38, 39, and 40 providing a hollow float body. The top wall 40 includes a recess providing member 41 having a hollow projection 42 providing the recess 25. The projection 42 has an upper opening 43 through which the tube 19 passes to enter the recess 25 so that the lower extremity 20 of the passage 36 can be located in the recess 25. The lower portion of the recess 25 is provided with a resilient pad 44 that is engagable with the lower extremity 20 to aid in closing the lower extremity 20 by engagement therewith.

The bottom wall 40 has attached to it a hollow projection 45 that receives the tube 22. More particularly the projection 45 has an opening 46 through which the tube 22 projects to have its upper extremity 23 engagable by a resilient pad 47 held in position by the projection 45. When engaged by the pad 47, the extremity 23 is closed.

Figure 4:
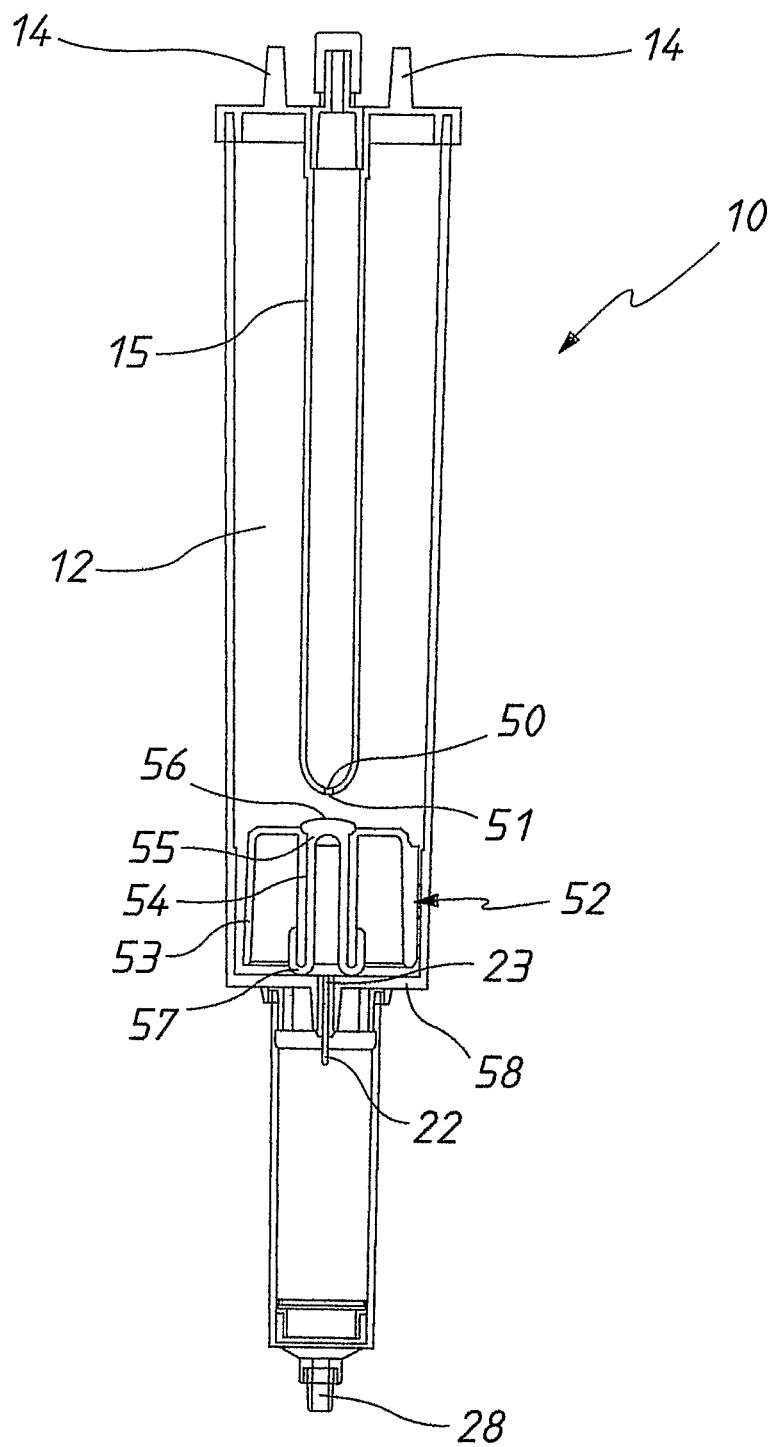
FIG. 4 is a schematic exploded sectioned side elevation of portion of the burette of FIG. 3.
Figure 5:
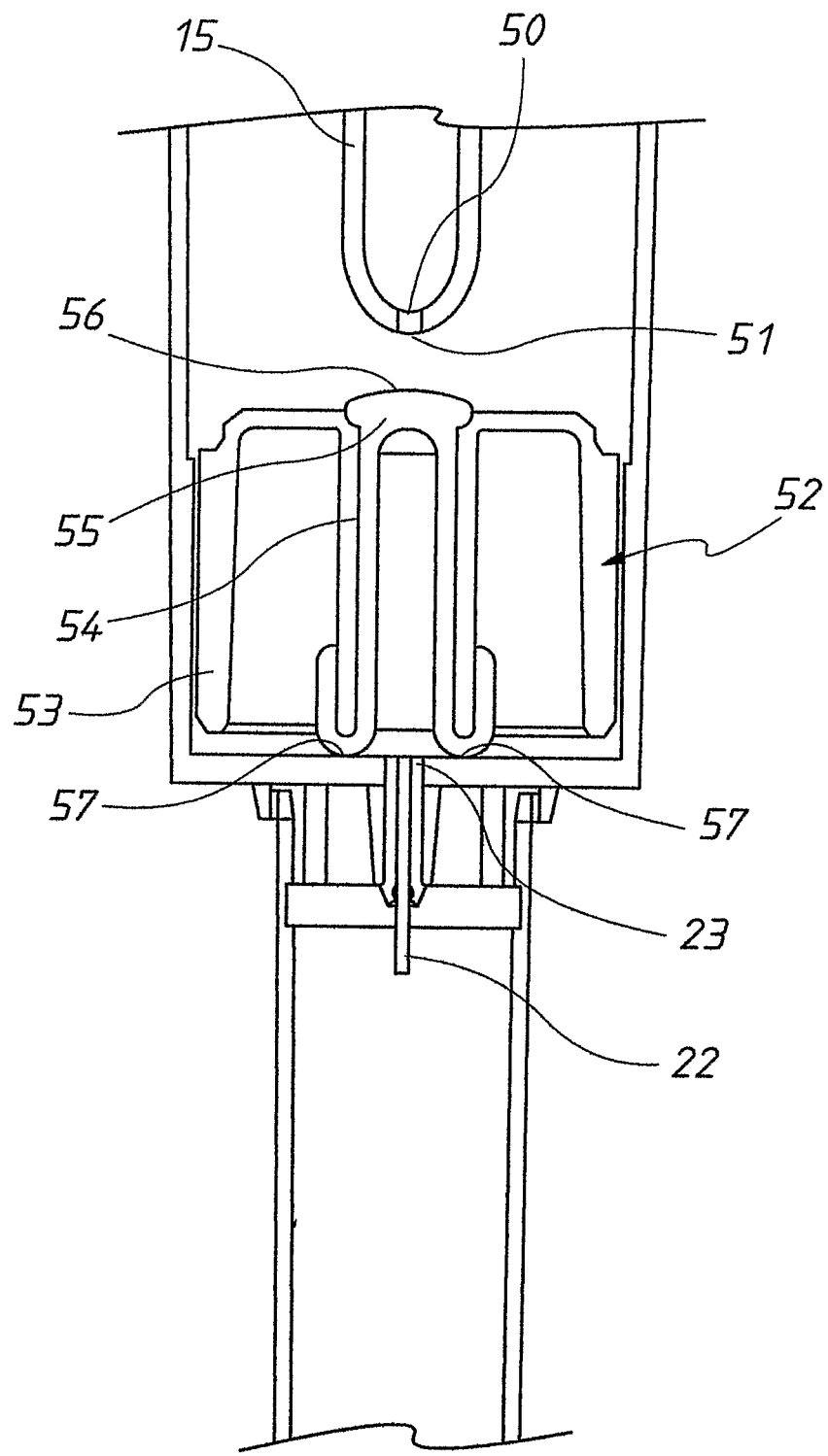
FIG. 5 is a schematic sectioned isometric view of a modification of the burette of FIG. 2.

In the embodiment of FIGS. 4 and 5, the stem 15 is provided at its lower end with a passage 50 having a lower extremity 51 closed by the float valve 52. The float valve 52 has a hollow body 53 of generally annular configuration providing a generally longitudinal central passage 54. Located in the passage 54 extending from a top wall 62 is a resilient valve member 55 having an upper extremity 56 located at the top wall 62 and (providing a first closure member) that is engaged with the lower extremity 51 of the passage 50 to close the passage 50. The lower portion of the resilient valve member 54 has an annular sealing portion 57 (second closure member) that engages the bottom wall 58 through which the tube 22 projects so that the upper extremity is sealingly surrounded by the portion 57 so as to be closed thereby. The valve float 52 moves between the passage 50 and tube 22 in accordance with liquid level within the chamber 12. When at its upper limit the lower extremity 51 is closed, while at its lowest most extremity the tube 52 is closed by being isolated from the chamber 12. Accordingly the position of the valve float 52 regulates liquid level within the chamber 12.

Figure 6:
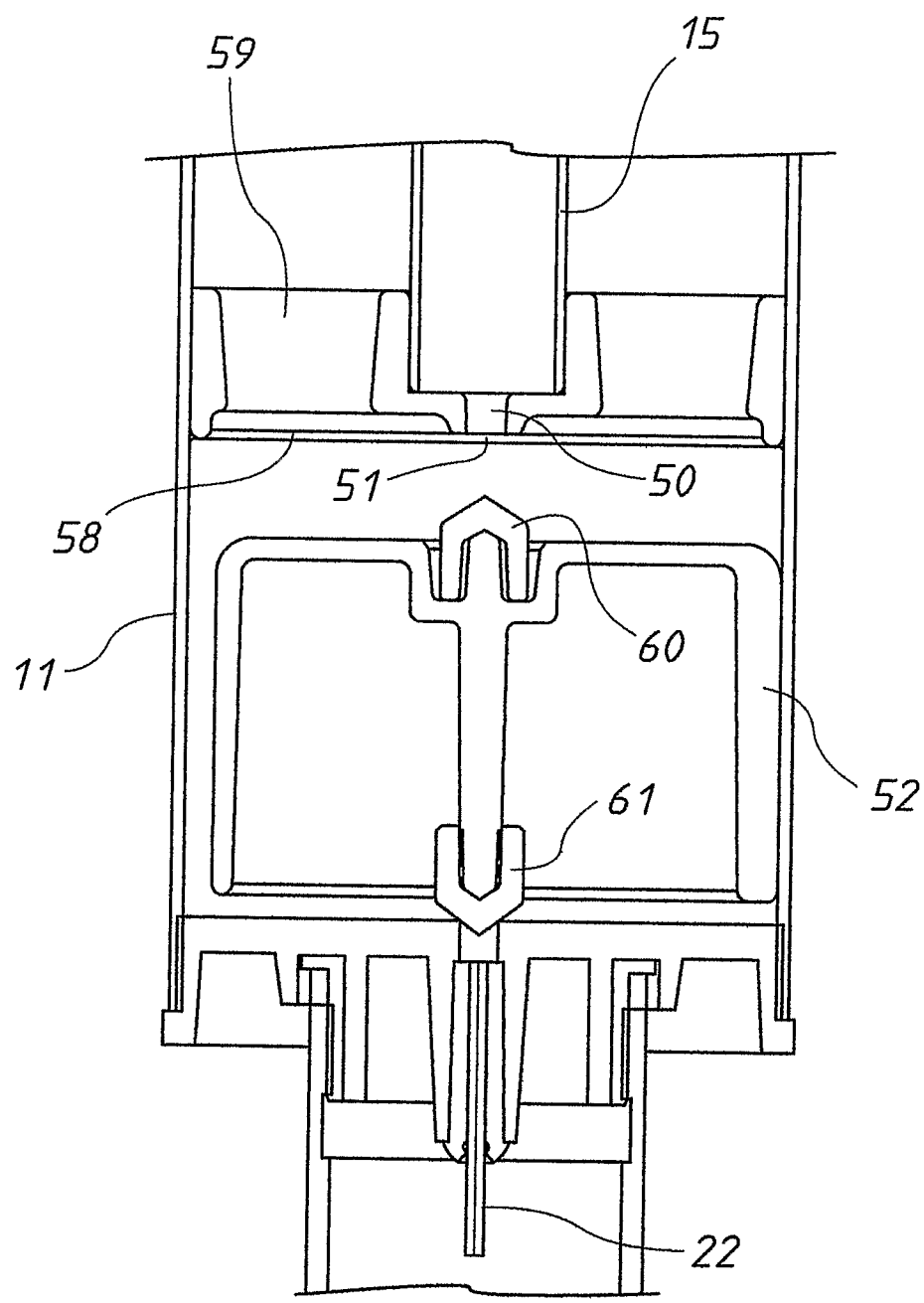
FIG. 6 is a schematic sectioned side elevation of the modified burette of FIG. 5.

In the embodiment of FIG. 6, the lower end of the stem 15 is supported by fins 58 extending to a rim 59 that engages the body 11. The valve float 52 has resilient pads 60 and 61 (first and second closure members), with the pads 60 being provided to close the passage 50 and the pad 61 provided to close the tube 22.

The pads 60 and 61 are located on the longitudinal axis 29, together with the extremity 50 and tube 22.

The invention claimed is:

1. A burette comprising:
    an elongated hollow body having a longitudinal axis that is to be generally vertically oriented during use, the body including a first chamber to receive a liquid to be dispensed by the burette;
    an inlet passage extending inwardly of the first chamber so as to terminate with an end extremity in the first chamber via which liquid is delivered to the first chamber;
    an outlet extending from the first chamber, the outlet being located below the inlet extremity; and
    a float valve located between the inlet passage and outlet and movable therebetween in response to changing liquid levels in the first chamber, the float valve including a hollow floatation body enclosing a second chamber, the hollow floatation body including a top wall closing the second chamber and having a recess to hold liquid, the recess being vertically aligned with said extremity so that when liquid level in first chamber is above a predetermined level the extremity is located below liquid level in the recess to at least inhibit flow to the first chamber through the passage, with the liquid level in the first chamber falling below a predetermined level causing the float valve to engage the outlet to close the outlet to prevent further liquid from leaving the first chamber.

2. The burette of claim 1, wherein the inlet passage is provided by a tube.

3. The burette of claim 2, wherein the first chamber is vertically elongated with the inlet further including a hollow stem having a lower end within which the tube is mounted, with the stem having an upper end to which a supply of the liquid is to be attached.

4. The burette of claim 1, further comprising a guide within which the float valve is located so as to be guided thereby for generally vertical movement between an upper position at which the extremity is located in the recess, and a lower extremity closing the outlet.

5. The burette of claim 4, wherein the guide provides a socket within which the float valve is located when closing the outlet.

6. A burette comprising:
   an elongated hollow main body having a longitudinal axis that is to be generally vertically oriented during use, the elongated hollow main body including a first chamber to receive a liquid to be dispensed by the burette;
   an inlet passage extending inwardly of the first chamber so as to terminate with an end extremity in the first chamber via which liquid is delivered to the first chamber;
   an outlet extending from the first chamber, the outlet being located below the inlet extremity; and
   a float valve located between the inlet passage and the outlet and movable therebetween in response to change in liquid levels in the first chamber, the float valve having a hollow float body including a second chamber with an upper portion, the hollow float body providing floatation and, a first closure member mounted in the hollow float body to engage the end extremity to close the passage, and a second closure member mounted in the hollow float body to engage the outlet to close the outlet, so that upon the liquid level in the first chamber being above a predetermined level the first closure member closes the end extremity, while when liquid level in the first chamber falls below a further predetermined level, the second closure member closes the outlet, and
   wherein the hollow float body has a top wall, closing the upper portion of the second chamber, and at which the first closure member is located, and the first closure member and the second closure member are resilient pads with the second closure member providing an annular sealing portion to surround the outlet to thereby isolate the outlet from the first chamber so that the outlet is effectively closed.

7. The burette of claim 6, wherein the first and second closure members are aligned along the longitudinal axis.

8. The burette of claim 6, wherein the second closure member directly engages the outlet.

* * * * *